United States Patent [19]

Bender et al.

[11] 3,949,076

[45] Apr. 6, 1976

[54] N-(HETEROCYCLIC-ALKYL)-9-XANTHENYLAMINES

[75] Inventors: Paul E. Bender, Willingboro, N.J.; Bernard Loev, Broomall; Carl D. Perchonock, Philadelphia, both of Pa.

[73] Assignee: SmithKline Corporation, Philadelphia, Pa.

[22] Filed: May 29, 1975

[21] Appl. No.: 582,055

[52] U.S. Cl. ......... 424/251; 260/256.4 H; 260/309; 260/309.6; 424/273
[51] Int. Cl.² ............ C07D 233/16; C07D 233/60; C07D 239/06
[58] Field of Search.......... 260/309, 309.6, 256.4 H; 424/273, 251

[56] References Cited
UNITED STATES PATENTS

| | | | |
|---|---|---|---|
| 3,042,674 | 7/1962 | Faust et al. | 260/309.6 |
| 3,558,779 | 1/1971 | Adams et al. | 424/283 |
| 3,681,373 | 8/1972 | Adams et al. | 260/309 |
| 3,717,655 | 2/1973 | Godefroi et al. | 260/309 |
| 3,736,098 | 5/1973 | Kataoka et al. | 260/309.6 |

OTHER PUBLICATIONS

Adams et al. III Chem. Abst. 1970 Vol. 72, No. 121369x.
Adams et al. IV Chem. Abst. 1970, Vol. 73, No. 120633n.
Schwan Chem. Abst. 1968, Vol. 68, No. 39536h.

*Primary Examiner*—Natalie Trousof
*Attorney, Agent, or Firm*—Joan S. Keps; Richard D. Foggio; William H. Edgerton

[57] ABSTRACT

The compounds are N-(imidazolylalkyl, imidazolinylalkyl and tetrahydropyrimidylalkyl)-9-xanthenylamines which have gastric acid secretion inhibitory activity.

8 Claims, No Drawings

N-(HETEROCYCLIC-ALKYL)-9-XANTHENYLAMINES

This invention relates to new N-(imidazolylalkyl), imidazolinylalkyl and tetrahydropyrimidylalkyl)-9-xanthenylamines having pharmacological activity. In particular, these compounds inhibit gastric acid secretion.

The compounds of this invention are represented by the following formula:

FORMULA I

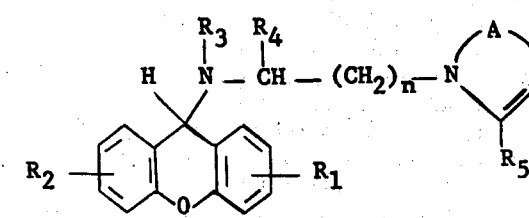

in which:

A is —CH=CH—, —CH$_2$CH$_2$— or —CH$_2$CH$_2$CH$_2$—;
R$_1$ is hydrogen, halogen, hydroxy, lower alkyl or lower alkoxy;
R$_2$ is hydrogen, halogen, lower alkyl or lower alkoxy;
R$_3$, R$_4$ and R$_5$ are hydrogen or lower alkyl and
n is 1 to 3 or a pharmaceutically acceptable acid addition salt thereof.

Preferably, in the compounds of Formula I, R$_1$ and R$_2$, being the same or different, are hydrogen, chloro, methyl or methoxy.

Particularly preferred compounds of this invention are represented by Formula I in which R$_1$ and R$_2$ are hydrogen and R$_3$, R$_4$ and R$_5$ are hydrogen or methyl.

Also, in preferred compounds of this invention, A is —CH=CH— or —CH$_2$CH$_2$—.

Particular compounds of this invention are N-[2-(1-imidazolyl)ethyl]-9-xanthenylamine and N-{2-[2-methyl-1-(2-imidazolinyl)]ethyl}-9-xanthenylamine.

Compounds in which the groups in the definition of A in Formula I above have one or two lower alkyl substituents, such as methyl, are prepared and used as are the unsubstituted compounds described herein.

The compounds of this invention produce inhibition of gastric acid secretion. This activity is demonstrated by administration to pylorus ligated rats at doses of about 30 to 50 mg./kg. orally and at about 5 to 50 mg./kg. intraduodenally. Also, this activity is demonstrated by administration to chronic gastric fistula rats at doses of about 30 mg./kg. orally and to chronic gastric fistula monkeys at doses of about 7.5 to about 15 mg./kg. by intragastric administration. In these procedures, compounds which produce an increase in gastric pH or a decrease in volume of gastric juice or both are considered active.

These compounds show antiulcer activity, for example in the restraint-stress method in which an oral administration to rats at doses of about 10 to 20 mg./kg. these compounds inhibit the development of experimental ulcers.

These compounds which inhibit gastric acid secretion are useful in treating gastric and duodenal ulcer disease and other conditions involving gastric acid hypersecretion.

The compounds of this invention are prepared by the following procedures:

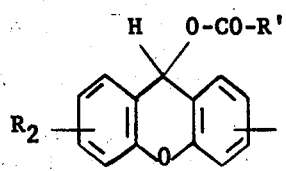

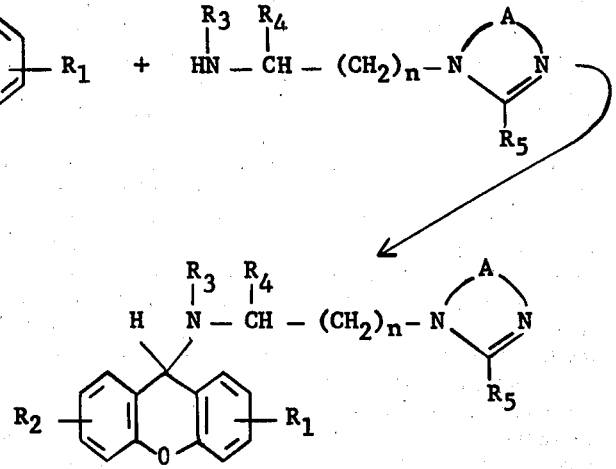

The terms A, R$_1$, R$_2$, R$_3$, R$_4$, R$_5$ and n are as defined above and R' is lower alkyl, preferably methyl.

According to the above procedure, a 9-xanthenyl alkanoate is reacted with an aminoalkylimidazole, imidazoline or tetrahydropyrimidine. The reaction is preferably carried out in an inert solvent such as benzene or toluene, at elevated temperature, conveniently at reflux temperature.

The 9-xanthenyl alkanoate starting materials are either known to the art or are prepared from xanthydrols by reacting the xanthydrol with a lower alkyl isocyanate to give a 9-lower alkylcarbamoyloxyxanthene and reacting that intermediate with a lower alkanoic acid.

The xanthydrols are either known to the art or are prepared by the following procedure. A 2-halobenzoic acid is reacted with a phenol preferably in the presence of a base such as potassium carbonate and in the presence of cuprous iodide and copper bronze. The resulting 2-phenoxybenzoic acid is cyclized by reacting with acid for example polyphosphoric acid. The resulting xanthone is reduced, for example using sodium amalgam in ethanol, to give the xanthydrol.

The 1-aminoalkyl)imidazole, imidazoline and tetrahydropyrimidine starting materials are either known to the art or are prepared by known procedures. For example, an imidazole is treated with sodium hydroxide and silver nitrate and the resulting silver salt of the imidazole is reacted with $Cl(CH_2)_n$—$CO$—$R_4$ and the resulting 1-[$R_4$—$CO$—$(CH_2)_n$]—imidazole is hydrogenated with $R_3NH_2$ in ethanol in the presence of platinum oxide catalyst to give the 1-(aminoalkyl)imidazoles.

The 1-(aminoalkyl)imidazolines and tetrahydropyrimidines are prepared by reacting a nitrile, acid or ester with ethylene or propylene diamine and reacting the resulting imidazoline or tetrahydropyrimidine with $Cl(CH_2)_n$—$CO$—$R_4$ to give 1-[$R_4$-$CO$-$(CH_2)_n$]-imidazoline or tetrahydropyrimidine and hydrogenating with $R_3NH_2$ as described above for the preparation of the imidazole intermediates.

The pharmaceutically acceptable, acid addition salts of the compounds of Formula I are formed with organic and inorganic acids by methods known to the art. The base is reacted with an organic or inorganic acid in aqueous miscible solvent, such as acetone or ethanol, with isolation of the salt by concentration and cooling or in aqueous immiscible solvent, such as ethyl ether or chloroform, with the desired salt separating directly. Exemplary of such organic salts are those with maleic, fumaric, benzoic, ascorbic, pamoic, succinic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids as well as with the 8-halotheophyllines, for example, 8-bromotheophylline. Exemplary of such inorganic salts are those with hydrochloric, hydrobromic, sulfuric, sulfamic, phosphoric and nitric acids. Of course, these salts may also be prepared by the classical method of double decomposition of appropriate salts which is well-known to the art.

Preferably, the compounds are administered in conventional dosage forms prepared by combining an appropriate dose of the compound with standard pharmaceutical carriers.

Pharmaceutical compositions having gastric acid secretion inhibitory activity, in dosage unit form, comprising a pharmaceutical carrier and a gastric acid secretion inhibiting amount of a compound of Formula I or a pharmaceutically acceptable acid addition salt thereof are objects of this invention.

The pharmaceutical carrier may be for example a solid or a liquid. Exemplary of solid carriers are lactose, magnesium stearate, terra alba, sucrose, talc, stearic acid, gelatin, agar, pectin, acacia or cocoa butter. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example the preparation may take the form of tablets, capsules, powders, suppositories, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The methods of inhibiting gastric acid secretion in accordance with this invention comprise administering internally to an animal an effective amount of a compound of Formula I or a pharmaceutically acceptable acid addition salt thereof. The acitve ingredients will preferably be administered in dosage unit form as described above.

The compounds of this invention will be administered in a daily dosage regimen of from about 10 mg. to about 2 g., preferably from about 25 mg. to about 1 g. Advantageously, equal doses will be administered one to four times per day. Dosage units will contain from about 10 mg. to about 500 mg., preferably from about 25 mg. to about 300 mg., of the active ingredient.

When administration is carried out as described above, gastric acid secretion is inhibited.

One skilled in the art will recognize that in determining the amounts of the active ingredients in the claimed compositions and used in the claimed methods, the activity of the chemical ingredient as well as the size of the host animal must be considered.

The terms "lower alkyl" and "lower alkoxy" where used herein denote groups having, preferably, 1–4 carbon atoms and "halogen" denotes chloro, bromo or fluoro.

The following examples are not limiting but are illustrative of the invention.

EXAMPLE 1

Methyl isocyanate (20 g.) was added slowly, with stirring, to a filtered solution of 30 g. of xanthydrol in 100 ml. of anhydrous triethylamine. After standing for 40 minutes to a 20° C. water bath, the mixture was filtered. The collected solid was washed with anhydrous diethyl ether and dried in vacuo to give 9-(N-methylcarbamoyloxy)xanthene.

To 15 g. of 9-(N-methylcarbamoyloxy)xanthene, suspended in 200 ml. of dry ether, was added 18 ml. of glacial acetic acid with stirring. After one hour, the lower acid layer was removed. The ether phase was then cooled, neutralized with cold aqueous sodium bicarbonate, dried over anhydrous magnesium sulfate and concentrated in vacuo. The residue was recrystallized from benzene-hexane to give 9-acetoxyxanthene, m.p. 109°–112° C.

A solution of 1.86 g. of 1-(2-aminoethyl)imidazole and 4.0 g. of 9-acetoxyxanthene dissolved in 100 ml. of dry benzene was refluxed for 24 hours. After cooling the solution was washed with 5% aqueous sodium carbonate solution and water, then dried over anhydrous sodium sulfate, filtered and concentrated in vacuo. The residue was redissolved in ether and deposited white crystals which were filtered and recrystallized from benzene-hexane to give N-[2-(1-imidazolyl)ethyl]-9-xanthenylamine, m.p. 90°–92° C.

EXAMPLE 2

A mixture of 7.2 g. of 9-acetoxyxanthene and 4.0 g. of 1-(2-aminoethyl)-2-methyl-2-imidazoline in 125 ml. of dry benzene was refluxed for 12 hours. The mixture was then cooled, the solvent was removed in vacuo, and the residue was dissolved in methylene chloride. This solution was washed with saturated aqueous sodium bicarbonate solution, dried over sodium sulfate, filtered, and concentrated in vacuo. The residue was chromatographed over alumina eluting with methanol. Concentration of the methanol eluate gave N-{2-[2-methyl-1-(2-imidazolinyl)]ethyl}-9-xanthenylamine, m.p. 82°–85° C.

EXAMPLE 3

To a stirred solution of 30 g. of imadazole and 16 g. of sodium hydroxide in 700 ml. of water is added dropwise 68 g. of silver nitrate in 250 ml. of water. After stirring for 20 minutes, the silver imidazole is filtered off and dried.

A mixture of 35.0 g. of silver imidazole, 21.3 g. of 4-chloro-2-butanone and 250 ml. of xylene is refluxed for four hours. The liquid is decanted and the solvent removed in vacuo to give 1-(3-oxobutyl)imidazole.

A suspension of 0.35 g. of platinum oxide in 30 ml. of absolute ethanol is hydrogenated at 50 p.s.i. for one hour. To this is added a mixture of 13.8 g. of 1-(3-oxobutyl)-imidazole, 6.2 g. of methylamine and 60 ml. of ethanol. The mixture is shaken under ca. 50 p.s.i. of hydrogen until one equivalent is absorbed. Filtration of the catalyst and removal of solvent in vacuo gives 1-(3-methylaminobutyl)-imidazole.

By the procedure of Example 1, 1-(3-methylaminobutyl)imidazole and 9-acetoxyxanthene in dry benzene are refluxed for 24 hours to give, after working up as in Example 1, N-[3-(1-imidazolyl)-butyl]-N-methyl-9-xanthenylamine.

EXAMPLE 4

A mixture of 4.1 g. of acetonitrile and 23.2 g. of 2-aminoethylammonium tosylate is heated in a sealed tube at ca. 190° C. for four hours. It is then dissolved in water, neutralized with 1N sodium hydroxide and extracted with chloroform. The extracts are dried, then the solvent is removed in vacuo to give as the residue 2-methyl-2-imidazoline.

A mixture of 8.4 g. of 2-methyl-2-imidazoline and 9.25 g. of chloroacetone is refluxed in 100 ml. of acetone for two hours. The solvent is removed in vacuo, and the residue is taken up in water and neutralized with 1N sodium hydroxide. Extracting with chloroform, drying and removing the solvent in vacuo gives 1-(2-oxopropyl)-2-methyl-2-imidazoline.

A suspension of 0.20 g. of platinum oxide in 20 ml. of absolute ethanol is hydrogenated at 50 p.s.i. for one hour. To this is added a mixture of 7.0 g. of 1-(2-oxopropyl)-2-methyl-2-imidazoline, 3.1 g. of methylamine and 30 ml. of ethanol. The mixture is shaken under ca. 50 p.s.i. of hydrogen until one equivalent is absorbed. Filtration of the catalyst and removal of solvent in vacuo gives 1-(2-methylaminopropyl)-2-methyl-2-imidazoline.

Refluxing a mixture of the above prepared imidazoline and 9-acetoxyxanthene in dry benzene for 12 hours and working up by the procedure of Example 2 gives N-{2-[2-methyl-1-(2-imidazolinyl)]propyl -N-methyl-} 9-xanthenylamine.

EXAMPLE 5

By the procedure of Example 1, using in place of 1-(2-aminoethyl)imidazole the following:
1-(2-aminoethyl)-2-isopropylimidazole
1-(3-aminopropyl)imidazole
1-(3-aminopropyl)-2-methylimidazole
1-(3-aminopropyl)-2-ethylimidazole the products obtained are, respectively:
N-[2-(2-isopropyl-1-imidazolyl)ethyl]-9-xanthenylamine
N-[3-(1-imidazolyl)propyl]-9-xanthenylamine
N-[3-(2-methyl-1-imidazolyl)propyl]-9-xanthenylamine
N-[3-(2-ethyl-1-imidazolyl)propyl]-9-xanthenylamine.

EXAMPLE 6

Using, in the procedure of Example 2, the following in place of 1-(2-aminoethyl)-2-methyl-2-imidazoline:
1-(2-aminoethyl)-2-imidazoline
1-(2-aminoethyl)-2-ethyl-2-imidazoline
1-(2-aminoethyl)-2-propyl-2-imidazoline
1-(3-aminopropyl)-2-methyl-2-imidazoline
1-(3-aminopropyl)-2-ethyl-2-imidazoline the following products are obtained, respectively:
N-{2-[1-(2-imidazolinyl)]ethyl}-9-xanthenylamine
N-{2-[2-ethyl-1-(2-imidazolinyl)]ethyl}-9-xanthenylamine
N-{2-[2-propyl-1-(2-imidazolinyl)]ethyl}-9-xanthenylamine
N-{3-[2-methyl-1-(2-imidazolinyl)]propyl}-9-xanthenylamine
N-{3-[2-ethyl-1-(2-imidazolinyl)]propyl}-9-xanthenylamine.

EXAMPLE 7

Using, in the procedure of Example 1, the following in place of xanthydrol:
2-chloroxanthydrol
3-chloroxanthydrol
4-chloroxanthydrol
1-chloroxanthydrol
3-fluoroxanthydrol
2-bromoxanthydrol the following products are obtained, respectively:
N-[2-(1-imidazolyl)ethyl]-2-chloro-9-xanthenylamine
N-[2-(1-imidazolyl)ethyl]-3-chloro-9-xanthenylamine
N-[2-(1-imidazolyl)ethyl]-4-chloro-9-xanthenylamine
N-[2-(1-imidazolyl)ethyl]-1-chloro-9-xanthenylamine
N-[2-(1-imidazolyl)ethyl]-3-fluoro-9-xanthenylamine
N-[2-(1-imidazolyl)ethyl]-2-bromo-9-xanthenylamine.

EXAMPLE 8

By the procedure of Example 1, the following substituted xanthydrols are converted to the corresponding substituted 9-acetoxyxanthenes:
3-methylxanthydrol
2-ethoxyxanthydrol
2,7-dibromoxanthydrol.

Reacting these substituted 9-acetoxyxanthenes with 1-(2-aminoethyl)-2-methyl-2-imidazoline by the procedure of Example 2 gives the following products, respectively:
N-{2-[2-methyl-1-(2-imidazolinyl)]ethyl}-3-methyl-9-xanthenylamine
N-{2-(2-methyl-1-(2-imidazolinyl))ethyl}-2-ethoxy-9-xanthenylamine
N-{2-[2-methyl-1-(2-imidazolinyl)]ethyl}-2,7-dibromo-9-xanthenylamine.

EXAMPLE 9

Using, in the procedure of Example 1, the following substituted xanthydrols in place of xanthydrol:
2-methylxanthydrol
2-ethylxanthydrol
2-t-butylxanthydrol
3-methoxyxanthydrol
1,7-dimethoxyxanthydrol 1,8-dimethylxanthydrol
the following products are obtained, respectively:
- N-[2-(1-imidazolyl)ethyl]-2-methyl-9-xanthenylamine
- N-[2-(1-imidazolyl)ethyl]-2-ethyl-9-xanthenylamine
- N-[2-(1-imidazolyl)ethyl]-2-t-butyl-9-xanthenylamine
- N-[2-(1-imidazolyl)ethyl]-3-methoxy-9-xanthenylamine
- N-[2-(1-imidazolyl)ethyl]-1,7-dimethoxy-9-xanthenylamine
- N-[2-(1-imidazolyl)ethyl]-1,8-dimethyl-9-xanthenylamine.

EXAMPLE 10

A mixture of 1-(3-oxobutyl)imidazole, ethylamine and ethanol is hydrogenated using platinum oxide as catalyst, by the procedure of Example 3, to give 1-(3-ethylaminobutyl)imidazole.

Refluxing 1-(3-ethylaminobutyl)imidazole with 9-acetoxyxanthydrol in dry benzene by the procedure of Example 1 gives N-[3-(1-imidazolyl)butyl]-N-ethyl-9-xanthenylamine.

In the same manner, using propylamine and butylamine in place of ethylamine, the corresponding N-propyl and N-butyl xanthenylamines are obtained.

EXAMPLE 11

A suspension of 25 g. of 3-chloro-6-methoxyxanthone in 175 ml. of 95% aqueous ethanol is poured into a flask containing sodium amalgam prepared from 9.0 g. of sodium and 55 ml. of mercury. The flask is stoppered and shaken vigorously for 20 minutes with intermittant venting. The amalgam is then allowed to settle and the ethanolic suupernatant is decanted into 1.5 liters of water. The precipitate is filtered from the resulting mixture, washed with water, and air dried to yield 3-chloro-6-methoxyxanthydrol.

Using 3-chloro-6-methoxyxanthydrol in place of xanthydrol in the procedure of Example 1 gives N-[2-(1-imidazolyl)ethyl]-3-chloro-6-methoxy-9-xanthenylamine.

Similarly, using the following xanthones as starting materials:
- 2-propylxanthone
- 3,6-dichloroxanthone
- 3-methoxy-6-methylxanthone
- 6-methoxy-2-methylxanthone
- 3-hydroxyxanthone
- 2-hydroxyxanthone
- 6-hydroxy-2-methylxanthone the products obtained are, respectively:
- N-[2-(1-imidazolyl)ethyl]-2-propyl-9-xanthenylamine
- N-[2-(1-imidazolyl)ethyl]-3,6-dichloro-9-xanthenylamine
- N-[2-(1-imidazolyl)ethyl]-3-methoxy-6-methyl-9-xanthenylamine
- N-[2-(1-imidazolyl)ethyl]-6-methoxy-2-methyl-9-xanthenylamine
- N-[2-(1-imidazolyl)ethyl]-3-hydroxy-9-xanthenylamine
- N-[2-(1-imidazolyl)ethyl]-2-hydroxy-9-xanthenylamine
- N-[2-(1-imidazolyl)ethyl]-6-hydroxy-2-methyl-9-xanthenylamine.

EXAMPLE 12

A mixture of 5.6 g. of ethyl orthoformate and 24.6 g. of 3-aminopropylammonium tosylate is heated in a sealed tube at 190° C. for four hours. The mixture is then dissolved in water, neutralized with 1N sodium hydroxide and extracted with chloroform. The extracts are dried and the solvent is removed in vacuo to give, as the residue, 1,4,5,6-tetrahydropyrimidine.

A mixture of 8.4 g. of 1,4,5,6-tetrahydropyrimidine and 7.8 g. of chloroacetaldehyde is refluxed in 100 ml. of acetone for two hours. The solvent is removed in vacuo and the residue is taken up in water and neutralized with 1N sodium hydroxide. Extracting with chloroform, drying and removing the solvent in vacuo gives 1,4,5,6-tetrahydropyrimidine-1-acetaldehyde.

A suspension of 0.20 g. of Raney nickel, 6.3 g. of 1,4,5,6-tetrahydropyrimidine-1-acetaldehyde and 1.7 g. of ammonia in 50 ml. of ethanol is shaken under 20 atmospheres of hydrogen at 40° C. until one equivalent is absorbed. The catalyst is filtered off and the solvent is removed in vacuo to give 1-(2-aminoethyl)-1,4,5,6-tetrahydropyrimidine.

Refluxing 1-(2-aminoethyl)-1,4,5,6-tetrahydropyrimidine with 9-acetoxyxanthene in dry benzene and working up by the procedure of Example 1 gives N-{2-[1-(1,4,5,6-tetrahydropyrimidyl)]ethyl}-9-xanthenylamine.

By the same procedure, using acetic acid in place of ethyl orthoformate, the product is N-{2-[2-methyl-1-(1,4,5,6-tetrahydropyrimidyl)]ethyl}-9-xanthenylamine.

Also, by the same procedure, using valeric acid in place of ethyl orthoformate, the product is N-{2-[2-butyl-1-(1,4,5,6-tetrahydropyrimidyl)]ethyl}-9-xanthenylamine.

Using 4-chloro-2-butanone in place of chloroacetaldehyde in the above procedure, the product is N-{3[1-(1,4,5,6-tetrahydropyrimidyl)]butyl}-9-xanthenylamine.

Similarly, using 5-chloro-2-pentanone in place of chloroacetaldehyde, the product is N-{4-[1-(1,4,5,6-tetrahydropyrimidyl)]pentyl}-9-xanthenylamine.

EXAMPLE 13

By the procedure of Example 3, converting the following substituted imidazoles to the silver salts:
- 2-methylimidazole
- 2-ethylimidazole
- 2-propylimidazole
- 2-butylimidazole reacting with chloroacetaldehyde, hydrogenating the resulting imidazole-1-acetaldehydes with ammonia in ethanol and reacting the resulting 1-(2-aminoethyl)imidazoles with 9-acetoxyxanthene gives the following products:
- N-[2-(2-methyl-1-imidazolyl)ethyl]-9-xanthenylamine
- N-[2-(2-ethyl-1-imidazolyl)ethyl]-9-xanthenylamine
- N-[2-(2-propyl-1-imidazolyl)ethyl]-9-xanthenylamine
- N-[2-(2-butyl-1-imidazolyl)ethyl]-9-xanthenylamine.

EXAMPLE 14

Using, in the procedure of Example 3, the following in place of 4-chloro-2-butanone:
- 1-chloro-2-butanone
- 1-chloro-3-pentanone
- 1-chloro-2-pentanone 1-chloro-2-hexanone
1-chloro-3-hexanone
and using ammonia in place of methylamine the products are, respectively:

N-[2-(1-imidazolyl)butyl]-9-xanthenylamine
N-[3-(1-imidazolyl)pentyl]-9-xanthenylamine
N-[2-(1-imidazolyl)pentyl]-9-xanthenylamine
N-[2-(1-imidazolyl)hexyl]-9-xanthenylamine
N-[3-(1-imidazolyl)hexyl]-9-xanthenylamine.

EXAMPLE 15

Reacting N-[2-(1-imidazolyl)ethyl]-9-xanthenylamine with hydrogen chloride in ether gives the hydrochloride salt thereof.

Reacting with concentrated sulfuric acid in ether gives N-[2-(1-imidazolyl)ethyl]-9-xanthenylamine sulfate.

EXAMPLE 16

| Ingredients | Amounts |
| --- | --- |
| N-[2-(1-imidazolyl)ethyl]-9-xanthenylamine | 150 mg. |
| Lactose | 75 mg. |
| Magnesium stearate | 5 mg. |

The ingredients are mixed and filled into a hard gelatin capsule.

EXAMPLE 17

| Ingredients | Amounts |
| --- | --- |
| N-{2-[2-methyl-1-(2-imidazolinyl)]ethyl}-9-xanthenylamine | 200 mg. |
| Lactose | 100 mg. |

The ingredients are mixed and filled into a hard gelatin capsule.

What is claimed is:
1. A compound of the formula

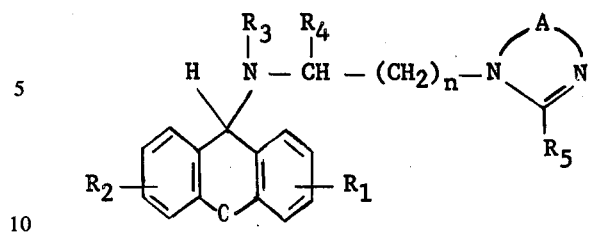

in which:
A is —CH=CH—, —CH$_2$CH$_2$— or —CH$_2$CH$_2$CH$_2$—;
R$_1$ is hydrogen, halogen, hydroxy, lower alkyl or lower alkoxy;
R$_2$ is hydrogen, halogen, lower alkyl or lower alkoxy;
R$_3$, R$_4$ and R$_5$ are hydrogen or lower alkyl and $n$ is 1 to 3
or a pharmaceutically acceptable acid addition salt thereof.

2. A compound of claim 1 in which R$_1$ and R$_2$, being the same or different, are hydrogen, chloro, methyl or methoxy.

3. A compound of claim 1 in which R$_1$ and R$_2$ are hydrogen and R$_3$, R$_4$ and R$_5$ are hydrogen or methyl.

4. A compound of claim 1 in which A is —CH=CH— or —CH$_2$CH$_2$—.

5. A compound of claim 1, said compound being N-[2-(1-imidazolyl)ethyl]-9-xanthenylamine.

6. A compound of claim 1, said compound being N-{2-[2-methyl-1-(2-imidazolinyl)]ethyl}-9-xanthenylamine.

7. A pharmaceutical composition having gastric acid secretion inhibitory activity comprising a pharmaceutical carrier and an effective amount of a compound of claim 1.

8. A method of inhibiting gastric acid secretion comprising administering to an animal an effective amount of a compound of claim 1.

* * * * *